(12) United States Patent
Minoda et al.

(10) Patent No.: US 9,671,377 B2
(45) Date of Patent: Jun. 6, 2017

(54) THIN-LAYER CHROMATOGRAPHY PLATE

(71) Applicant: DAICEL CORPORATION, Osaka-shi, Osaka (JP)

(72) Inventors: Toshiharu Minoda, Myoko (JP); Isamu Ikeda, Myoko (JP)

(73) Assignee: DAICEL CORPORATION, Osaka-shi, Osaka (JP)

(*) Notice: Subject to any disclaimer, the term of this patent is extended or adjusted under 35 U.S.C. 154(b) by 394 days.

(21) Appl. No.: 14/348,989

(22) PCT Filed: Oct. 4, 2012

(86) PCT No.: PCT/JP2012/075808
§ 371 (c)(1),
(2) Date: Apr. 1, 2014

(87) PCT Pub. No.: WO2013/051652
PCT Pub. Date: Apr. 11, 2013

(65) Prior Publication Data
US 2014/0248196 A1 Sep. 4, 2014

(30) Foreign Application Priority Data
Oct. 5, 2011 (JP) .................................. 2011-220998

(51) Int. Cl.
G01N 30/90 (2006.01)
G01N 30/92 (2006.01)
(Continued)

(52) U.S. Cl.
CPC ............ *G01N 30/92* (2013.01); *B01J 20/285* (2013.01); *B01J 20/286* (2013.01); *B01J 20/29* (2013.01);
(Continued)

(58) Field of Classification Search
CPC ................................ G01N 30/90; G01N 30/92
See application file for complete search history.

(56) References Cited

U.S. PATENT DOCUMENTS 3,591,805 A 7/1971 Schoeffel
5,306,645 A 4/1994 Yamamoto et al.
(Continued)

FOREIGN PATENT DOCUMENTS

JP 03-063567 3/1991
JP 05-232099 9/1993
WO WO 2011/149041 A1 * 12/2011

OTHER PUBLICATIONS

Chinese Office Action dated Sep. 28, 2014 with English translation (14 pages).
(Continued)

Primary Examiner — Jan Ludlow
(74) Attorney, Agent, or Firm — Flynn, Thiel, Boutell & Tanis, P.C.

(57) ABSTRACT

A TLC plate allows the separation and detection of target substances on one plate. The TLC plate is made up of a substrate, a separating medium layer stacked on the substrate, and a permeation layer discontinuously stacked on the separating medium layer and allows the permeation of a target substance separated in the separating medium layer, wherein the separating medium layer has a separating property for the target substance and an optical responsiveness for ultraviolet rays, and the permeation layer has an optical responsiveness different from that of the separating medium layer.

7 Claims, 3 Drawing Sheets (1)

(2)

(3)

(4)

(51) Int. Cl.
  *B01J 20/29*   (2006.01)
  *B01J 20/285*  (2006.01)
  *B01J 20/286*  (2006.01)
  *G01N 30/88*   (2006.01)
  *B01D 15/38*   (2006.01)

(52) U.S. Cl.
  CPC .. *B01D 15/3833* (2013.01); *G01N 2030/8877* (2013.01)

(56) References Cited

U.S. PATENT DOCUMENTS 9,234,881 B2 * 1/2016 Minoda
2003/0141252 A1 7/2003 Okamoto et al.
2011/0000852 A1 1/2011 Linford et al.

OTHER PUBLICATIONS

International Search Report for PCT/JP2012/075808 (1 page).
2-Dimensional Chiral TLC IA/IC, Daicel Corp. CPI Company, Sep. 2011 (on-line) (6 pages).
Supplementary European Search Report for PCT/JP2012/075808 dated Apr. 28, 2015 (5 pgs.).
Supplementary European Search Report for European Patent Application No. 12838756.0 dated Apr. 28, 2015 (5 pgs.).

\* cited by examiner (a)  (b)

(a)  (b)

(1)　　　　(2)　　　　(3)　　　　(4)

THIN-LAYER CHROMATOGRAPHY PLATE

BACKGROUND OF THE INVENTION

Field of the Invention

The present invention relates to a thin layer chromatography plate (hereinafter also referred to as "TLC plate") containing two types of layers having different optical responses to ultraviolet rays.

Description of the Related Art

Thin layer chromatography (hereinafter also referred to as "TLC") is a known method for separating and detecting specific substances in mixtures. Separation of substances by TLC is detected for example on the basis of differential optical responses between a separating medium layer and a substance to be detected, by subjecting developed spots of samples to irradiation of ultraviolet rays or colour development treatment using a chromogenic reagent.

Meanwhile known separating media for optical isomers include separating media containing polysaccharide derivatives such as phenyl esters of polysaccharides. When such separating media containing aromatic rings are used for the separating medium layers of TLC plates, a substance may not be detected by the irradiation of ultraviolet rays or colour development treatment using a chromogenic reagent.

In order to address such a problem, a TLC plate is known which contains, on the same substrate in parallel, a first separating medium layer that has a separating property for a target substance but does not have an optical responsiveness and a second separating medium layer that does not have the separating property but has an optical responsiveness (see, for example, Japanese Patent No. 3140138). In this TLC plate, a target substance in a sample is developed from the first separating medium layer to the second separating medium layer, and the spots separated in the first separating medium layer migrate to the second separating medium layer and are detected therein depending on the optical responsiveness thereof.

In this TLC plate, an extracted component in the samples that is easily adsorbable by the first separating medium layer may not sufficiently reach the second separating medium layer. In addition, because the migration speed of the spots of the target substance in the sample is generally different between the respective separating medium layers, the relative positions of the spots in the first separating medium layer may not be accurately maintained in the second separating medium layer. Accordingly this TLC plate may not allow the accurate detection of the separation in the first separating medium layer, leaving room for improvement in this point.

PRIOR ART DOCUMENT

Patent Document

Patent document 1: JP3140138 B

SUMMARY OF THE INVENTION

The present invention provides a TLC plate which allows the separation and detection of target substances in samples on one plate.

The present inventors have found that the above problem can be solved by stacking, on a TLC plate including a substrate and a separating medium layer, a permeation layer allowing the permeation of a target substance separated in the separating medium layer and having a different optical responsiveness from that of the separating medium layer, thereby completing the present invention.

Thus, the present invention provides a TLC plate including a substrate, a separating medium layer stacked on the substrate, and a permeation layer stacked on the separating medium layer and allowing the permeation of a target substance separated in the separating medium layer, wherein the separating medium layer has a separating property for the target substance and an optical responsiveness for ultraviolet rays or a chromogenic reagent, and the permeation layer has an optical responsiveness different from that of the separating medium layer.

The present invention also provides the TLC plate, wherein the permeation layer is discontinuously stacked along a development direction of the TLC plate.

The present invention also provides the TLC plate, wherein the permeation layer is stacked on the separating medium layer in a dotted manner.

The present invention also provides the TLC plate, wherein the permeation layer is stacked on the separating medium layer in the form of a series of strips intersecting a development direction of the TLC plate.

The present invention also provides the TLC plate, wherein the strips forming the series of strips have a shape selected from a straight line, a wavy line or a dashed line thereof.

The present invention also provides the TLC plate, wherein the permeation layer is stacked in the dotted manner such that an average diameter of dots is 0.01 to 5 mm and a pitch between dots is 0.015 to 5 mm.

The present invention also provides the TLC plate, wherein the permeation layer contains a porous material as a constituent.

The present invention also provides the TLC plate, wherein the separating medium layer contains, as a separating medium, a separating medium for an optical isomer.

The present invention also provides the TLC plate, wherein the separating medium for an optical isomer is a polysaccharide derivative having hydroxy or amino groups partly or totally replaced by any of an aromatic ester group, an aromatic carbamoyl group, an aromatic ether group and a carbonyl group.

The TLC plate of the present invention comprises the permeation layer allowing the permeation of a separated target substance stacked on the separating medium layer, the permeation layer having an optical responsiveness different from that of the separating medium layer, and thus allows the detection of the target substance permeated in the permeation layer by means of optical responsiveness, which substance may not be otherwise detected by means of optical responsiveness when it is in the separating medium layer. The TLC plate of the present invention allows the separation and detection of a target substance within one plate, and thus the complex procedures for separation and detection of a target substance are not required.

BRIEF DESCRIPTION OF THE DRAWINGS

FIG. 1 (*b*) is a view (photographic image) showing spots of Troeger's base and flavanone developed on the TLC plate 1;

FIG. 2 (*b*) is a view (photographic image) showing spots of Troeger's base and flavanone developed on the TLC plate 2;

DESCRIPTION OF THE PREFERRED EMBODIMENTS

Figure 1:
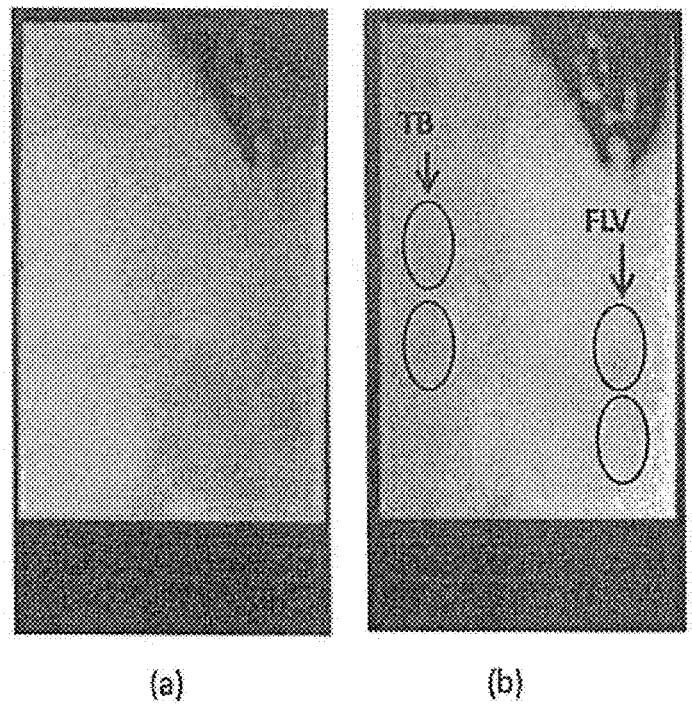
FIG. 1 (*a*) is a view of a TLC plate 1 of the present invention in which a permeation layer is stacked so as to cover the whole area of a separating medium layer.

The TLC plate of the present invention includes a substrate, a separating medium layer and a permeation layer allowing the permeation of a target substance separated in the separating medium.

The substrate may be a well known substrate for TLC. The substrate may include, for example, a flat plate of glass, resin, metal or paper. The substrate may have any shape without limitation and preferably has a rectangular shape which is usually used for TLC.

The separating medium layer in the TLC plate of the present invention is not particularly limited as long as it has a separating property for a target substance and an optical responsiveness for ultraviolet rays. The phrase "optical responsiveness for ultraviolet rays" as used herein refers to a luminescence by ultraviolet rays such as fluorescence or the absorption of ultraviolet rays. The TLC plate having a separating medium layer stacked on a substrate can be appropriately selected from well known TLC plates, and can be obtained by applying a slurry of a separating medium having the separating property and optical responsiveness on a substrate and drying the slurry to form the separating medium layer.

The separating medium may be a particulate separating medium. The particulate separating medium may include particles consisting of a separating medium and particles containing a separating medium held on a particulate carrier.

The separating medium may be either a low-molecular or high-molecular separating medium having an optical responsiveness. The low-molecular separating medium may include, for example, a ligand exchange-based separating media, charge transfer (n-n)-based separating media, hydrogen bond-based separating media, clathrate-based separating media, ionic bond-based separating media, intercalating separating media, crown ethers or derivatives thereof and cyclodextrins or derivatives thereof. The high-molecular separating medium may include, for example, polysaccharide derivatives, polyamides, polymethacrylate esters, polyacrylamides, proteins and tartaric acid derivatives.

The polysaccharide derivatives may include, for example, polysaccharide derivatives which are used as separating media for optical isomers and have hydroxy or amino groups partly or totally replaced by any of an aromatic ester group, an aromatic carbamoyl group, an aromatic ether group and a carbonyl group, which may include, for example, phenylcarbamate derivatives of cellulose, phenyl ester derivatives of cellulose, phenylcarbamate derivatives of amylose and phenyl ester derivatives of amylose. The phenyl groups in these derivatives may contain one or more substituents selected from the group consisting of hydrocarbons with 1 to 20 carbon atoms and halogens.

The carrier is preferably a porous material in view of improving the separation performance. The carrier may include, for example, synthetic polymers such as crosslinked polystyrenes, crosslinked acrylic polymers and epoxy polymers; polysaccharides such as cellulose and crosslinked and reinforced cellulose, crosslinked agarose, crosslinked dextran and crosslinked mannan; inorganic materials such as alumina, silica gel, mesoporous silica gel, zeolite, diatomaceous earth, molten silica, clay mineral, zirconia and metals.

The particle diameter of the separating medium can be selected according to the purpose of separation on the TLC plate. It is preferable that the particle diameter is generally 10 μm or more, more preferably 10 to 100 μm and still more preferably 20 to 100 μm. The particle diameter of the separating medium may be an average particle diameter measured on conventional particle diameter analyzers or may be a catalogue value. Meanwhile, when better separation performance of spots is required, such as upon monitoring synthetic reactions, a separating medium smaller than 10 μm may also be used. The separating medium used for such an application preferably has a particle diameter of 2 to 8 μm and more preferably 3 to 6 μm.

In case of preparing the separating medium layer, it may be prepared by a well known method for preparing TLC plates, for example, by applying a slurry containing the separating medium and an application solvent on the surface of a support using a spreader, or by spraying the slurry onto the surface of the support, or by dipping the support into the slurry containing the separating medium and the application solvent.

The application solvent may be water, an organic solvent and a mixed solvent thereof. The organic solvent may include, for example, alcohols such as methanol, ethanol and isopropanol; ketones such as acetone and ethyl methyl ketone; ethers such as tetrahydrofuran and dioxane; nitriles such as acetonitrile; sulfoxides such as dimethyl sulfoxide; sulfones such as sulfolane; esters such as ethyl acetate; amides such as dimethylformamide; hydrocarbons such as pentane, hexane and petroleum ether; aromatic hydrocarbons such as benzene, toluene and xylene; halogen-containing compounds such as methylene chloride, chloroform, bromoform, chlorobenzene and bromobenzene.

The application solvent is preferably a mixed solvent of water and a hydrosoluble organic solvent, more preferably a mixed solvent of water and an alcohol and still more preferably a mixed solvent of water and ethanol. The amount of the alcohol in the mixed solvent is preferably 0.1 to 50% by mass, more preferably 10 to 40% by mass and still more preferably 20 to 30% by mass.

The amount of the application solvent in the slurry can be selected according to the uniformity of the formed separating medium layer, the thickness of the layer and the economical viewpoint, and is preferably, relative to 100 parts by mass of the separating medium, 10 to 5,000 parts by mass, more preferably 50 to 1,000 parts by mass and still more preferably 100 to 300 parts by mass.

It is preferable that the slurry further contains a binder in view of improving the strength of the formed separating medium layer. The binder may be a component which can provide a binding property so as to form the layer of the separating medium on the surface of the substrate. The binder may include inorganic binders such as gypsum and colloidal silica; organic binders such as organic fibres, e.g. microfibrillated cellulose; thickeners, e.g. alkaline hydrosoluble copolymers, hydroxyethyl cellulose and carboxymethyl cellulose; polyvinyl alcohols and acrylic acids. One or more binders may be used.

The amount of the binder in the slurry can be appropriately selected according to the type of the binder in view of the strength of the formed separating medium layer and an appropriate ascending speed of the mobile phase in the separating medium layer. For example, when gypsum is used, the amount of the binder is preferably, relative to 100 parts by mass of the separating medium, 0.1 to 50 parts by mass, more preferably 5 to 30 parts by mass and still more preferably 10 to 20 parts by mass. When an organic binder is used such as carboxymethyl cellulose, the amount of the binder is preferably, relative to 100 parts by mass of the separating medium, 0.1 to 50 parts by mass, more preferably 0.5 to 10 parts by mass and still more preferably 1 to 3 parts by mass.

The permeation layer has an optical responsiveness different from that of the separating medium layer. The phrase "optical responsiveness different from . . . " means that one optical response resulting from the irradiation of ultraviolet rays or colour development using a chromogenic reagent is different from the other optical response so as to be optically discriminated from each other by means of colour or brightness.

The permeation layer is a layer to which at least a part of a component(s) contained in a spot in the separating medium layer permeates.

It is important that a constituent(s) of the permeation layer does not affect the separation performance of a target substance in the separating medium layer on the TLC plate, namely the distribution of the target substance between a mobile phase and the separating medium layer, in order to avoid a broad spot of the target substance on the TLC plate.

Therefore, when the separating medium layer is a separating medium supported on a carrier, a constituent of the permeation layer is preferably the same as the carrier.

It is preferable that the permeation layer stacked on the separating medium layer is discontinuously stacked along the development direction of the TLC plate, in order to reduce the bypass action which is an interaction between the separating medium layer and the permeation layer, avoid a broad spot of the target substance and thus obtain a preferable separation (hereinafter also referred to as a separation property). The phrase "discontinuously stacked" as used herein means that the permeation layer is not stacked continuously along the development direction of the TLC plate but stacked at intervals which may be regular or irregular intervals.

The interval is preferably 0.015 mm or more, more preferably 0.02 mm or more and particularly preferably 0.05 mm or more, in order to obtain sufficient resolution for the detection of the target substance permeated into the permeation layer.

On the other hand, in order to reduce an interaction with the separating medium layer due to the diffusion of the target substance into the permeation layer and secure sufficient separation of the target substance, the interval is preferably 4 mm or less, more preferably 3 mm or less and particularly preferably 2 mm or less.

In this case, the permeation layer preferably covers the area of the TLC plate of the present invention as viewed from above at a proportion of 0.1 to 90%, more preferably 10 to 80% and still more preferably 20 to 70%, in order to secure a sufficient area for the permeation and detection of the target material.

Due to the same reason, the permeation layer preferably has the proportion of the void volume (the sum of the void volume in materials (internal void) and the void volume between materials (external void)) relative to the total volume of the layer of 0.1 to 0.9 and more preferably 0.2 to 0.8.

The permeation layer in the TLC plate of the present invention is preferably stacked on the separating medium layer in a dotted manner. The term "dotted manner" as used herein is a pattern containing discontinuous multiple dots or small sections which respectively have a shape of, for example, a circle, an approximate circle, an approximate ellipse, approximate polygons, the respective sides thereof may be a straight line or a curve, such as an approximate triangle and an approximate quadrangle, and the size or density of the dots is not particularly limited. The dots preferably have a regular shape in order to obtain a uniform separation property of a target substance on the TLC plate. The dots are also preferably arranged in a regular manner.

Figure 5:
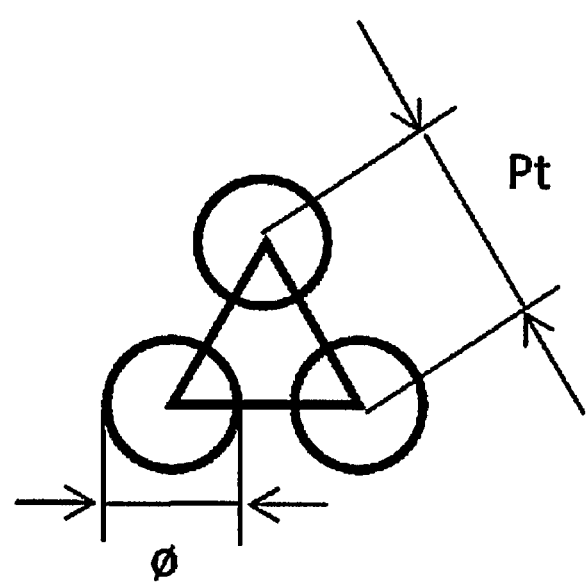
FIG. 5 is a diagram showing an example of a diameter (φ) and a pitch (Pt) of dots of a permeation layer stacked in a dotted manner in the TLC plate of the present invention.

The dots preferably have a shape of a circle or an approximate circle in view of the permeation of the target substance and are preferably arranged in a regular manner as shown in FIG. 5 in order to obtain the uniform separation property of the target substance on the TLC plate as described above.

When the dots have a circle shape, the average diameter thereof is preferably 0.01 to 5 mm in view of the permeation and separation properties of the target substance and is more preferably 0.01 to 4 mm, still more preferably 0.02 to 3 mm and particularly preferably 0.05 to 1 mm.

When the dots have a shape other than a circle, it is preferable that the average of the maximum diameter thereof is 0.02 to 6 mm form the same reasons as for the circular dots, and is more preferably 0.05 to 5 mm and still more preferably 0.05 to 1.5 mm.

The maximum diameter as used herein means the length of the longest axis for an ellipse, for example, and generally is the maximum distance between two parallel planes which sandwich the shape in question along an arbitrary direction as viewed from above.

When the permeation layer is stacked in a dotted manner, the interval (pitch) between dots is preferably 0.01 to 6 mm, more preferably 0.01 to 4 mm, still more preferably 0.02 to 3 mm and particularly 0.05 to 1.0 mm, in view of a reduction of an interaction with the separating medium layer and of the resolution upon the detection of the target substance permeating into the permeation layer.

When the dots have a circle shape, the pitch is preferably, form the same reason as above, 0.01 to 6 mm, more preferably 0.02 to 3 mm, still more preferably 0.05 to 1 mm and particularly preferably 0.06 to 1 mm.

The density of the dots, expressed as lines per inch (the number of dots per inch), is preferably 5 to 2000, more preferably 10 to 400 and still more preferably 20 to 300.

It is also a preferable embodiment wherein the permeation layer in the TLC plate of the present invention is stacked, other than in the dotted manner, in the form of a series of strips intersecting the development direction of the TLC plate. When the permeation layer is stacked in this manner, the separation property of the target substance can be sufficiently secured while the permeation of the target substance into the permeation layer can also be sufficient.

The strips that form the series of strips may be in the form of, for example, a straight line, a wavy line or a dashed line thereof. The width of the strip is not particularly limited, and may preferably be, in order to maintain the separation property of the target substance and obtain sufficient resolution for detection of the target substance, 0.01 to 15 mm and more preferably 0.02 to 10 mm.

The intervals between strips are not particularly limited but are preferably regular in order to obtain a uniform separation property of the target substance and are preferably 0.01 to 3 mm and more preferably 0.02 to 2 mm.

The permeation layer in the TLC plate of the present invention can contain a porous material as a constituent.

The porous material preferably has the pore volume, as measured by gas adsorption, of 0.1 ml/g or more, more preferably 0.2 ml/g or more and particularly preferably 0.3 to 0.9 ml/g, in order to secure sufficient permeation of the target substance.

The porous material having the above pore volume may be a commercial silica gel or ceramic products, which correspond to the preferable porous material described hereinbelow, having a catalogue value of the pore volume fulfilling the above range, or a silica-containing material which is subjected to the treatment with a hydrogen fluoride aqueous solution or an alkaline aqueous solution so as to adjust the pore volume thereof, or ceramics of which the pore volume is adjusted by adjusting the firing conditions during the granulation thereof or by treatment with an acid solution.

The porous material preferably has a particle diameter of 0.1 μm or more, more preferably 1 μm or more and particularly preferably 2 μm or more in order to avoid the aggregation of a slurry containing the porous material. The upper limit of the particle diameter of the porous material is preferably 100 μm or less, more preferably 70 μm or less and particularly preferably 50 μm or less, in view of the permeability upon screen printing of the slurry containing the porous material and the surface finish quality of the permeation layer.

The particle diameter of the porous material may be an average particle diameter measured on conventional particle diameter analyzers or may be a catalogue value.

The porous material used for the present invention may include the materials obtained by grinding silica gel, mesoporous silica gel, zeolite, cellulose, diatomaceous earth, molten silica, clay mineral, alumina, zirconia and other ceramics, e.g., sepiolite, attapulgite, palygorskite, talc mainly containing $SiO_2$ and MgO, kaolinite mainly containing $SiO_2$, montmorillonite and various clay minerals before granulation, optional acid treatment and firing. These materials may be commercial products which have the pore volume and particle diameter described above as catalogue values.

Among these, the materials having the above pore volume and particle diameter are preferred and silica gel is preferable in view of the compatibility with the solvent.

The porous material selected preferably does not affect the distribution of the target substance between the separating medium layer and the mobile phase in order to avoid a broad spot of the target substance on the TLC plate.

The permeation layer of the TLC plate of the present invention may contain as a constituent a fluorescent indicator or a chromogenic reagent per se as described hereinbelow. The permeation layer can also be formed by stacking a mixed composition comprising the fluorescent indicator or the chromogenic reagent, a binder and optionally a support such as glass, plastics, metals and ceramics having a particle diameter of 0.1 to 100 μm.

The amount of the binder in such a composition may be appropriately selected according to the type of the binder in view of the strength of the permeation layer formed and in view of reducing the bypass action in the permeation layer which is an interaction between the separating medium layer and the permeation layer. For example, when gypsum is used, the amount of the binder is preferably, relative to 100 parts by mass of the fluorescent indicator or the chromogenic reagent, 0.1 to 50 parts by mass, more preferably 0.5 to 30 parts by mass and still more preferably 1 to 20 parts by mass. When an organic binder is used, such as carboxymethyl cellulose, the amount of the binder is preferably, relative to 100 parts by mass of the fluorescent indicator or the chromogenic reagent, 0.1 to 50 parts by mass, more preferably 0.5 to 10 parts by mass and still more preferably 1 to 5 parts by mass.

When the support is used, the amount thereof is preferably, relative to 100 parts by mass of the fluorescent indicator or the chromogenic reagent, 0.1 to 0.9 parts by mass, more preferably 0.2 to 0.8 parts by mass and particularly preferably 0.3 to 0.7 parts by mass.

The permeation layer in the TLC plate of the present invention can be stacked by various methods. For example, the permeation layer containing the porous material as a constituent can be prepared by applying a slurry containing the porous material on the separating medium layer of the TLC plate and the drying thereof. The same method can be used for the permeation layer which is the fluorescent indicator or the chromogenic reagent per se as described hereinbelow or a composition containing the fluorescent indicator or the chromogenic reagent, the binder and optionally the support.

The permeation layer discontinuously stacked along the development direction of the TLC plate of the present invention can be stacked by using, for example, printing technology.

Printing technology may include silk screen printing and ink jet printing.

In silk screen printing, a silk screen plate can be used which has openings with the shape as described above for the manner of the stacking of the permeation layer (the one having discontinuous openings along the development direction of the TLC plate or the one having openings which are dots or a series of strips with various shapes). Silk screen printing is preferably used because the permeation layer can be stacked with a relatively low cost and simple procedures.

The silk screen plate is not particularly limited for the material thereof as far as it allows the use of a slurry containing the porous material as described hereinbelow as the printing ink.

Meanwhile, general ink jet printing techniques can be also used provided that the printing ink used is a slurry containing the porous material as described hereinbelow.

The permeation layer stacked by the application of the slurry or printing technology described above preferably has a thickness (average thickness) of 0.005 mm or more and still more preferably 0.01 mm or more in order to secure sufficient permeation and avoid an influence from the optical responsiveness of the separating medium layer upon the detection of spots of the target substance when the porous material is transparent or semi-transparent, for example.

The permeation layer preferably has a thickness (average thickness) of 0.2 mm or less and still more preferably 0.15 mm or less in view of the prevention of the diffusion of spots of the target substance.

The above techniques of the application and printing may be used for stacking the permeation layer on the separating medium layer, in which the slurry containing the porous material, a solution containing the fluorescent indicator or the chromogenic reagent, or a composition comprising the fluorescent indicator or the chromogenic reagent, a binder and optionally a support is prepared which can be used as an application solution or printing ink.

Materials used for the preparation of the slurry containing the porous material may include a solvent and optionally a binder. The solvent and the binder may be the same as those used for the formation of the separating medium layer.

The fluorescent indicator may include, for example, magnesium tungstate, manganese-containing zinc silicate and the like. The solution or slurry containing the fluorescent indicator may be prepared by using a solvent, for example, an ink solvent for screen printing such as organic solvents including alcohols, glycol ethers, hydrocarbons, ketones and esters. The solvent may include, for example, α-terpineol, butyl carbitol acetate, butyl carbitol, toluene, cyclohexane, methyl ethyl ketone and methyl propylene glycol. Appropriate solvents are selected with the consideration of physical properties such as fluidity, boiling point and evaporation speed so that the fluidity of the slurry is not deteriorated or a screen is not clogged during printing.

The chromogenic reagent may include an anisaldehyde solution, phosphomolybdic acid solution, iodine solution, ninhydrin solution, chameleon solution, DNPH solution, manganese chloride solution and bromocresol green solution.

When a composition comprising the fluorescent indicator or the chromogenic reagent, a binder and optionally a support is used, the composition containing the binder may be dissolved or suspended in the solution of the fluorescent indicator or the chromogenic reagent to obtain an application solution or printing ink.

When the permeation layer contains the porous material as a constituent, the solvent for a slurry containing the porous material may be an organic solvent alone selected from alcohols, glycol ethers, hydrocarbons, ketones and esters. When an alcohol is used, a mixed solvent of a water-soluble organic solvent and water is preferable, and a mixed solvent of an alcohol and water is more preferable. The amount of the alcohol in the mixed solvent is preferably 0.1 to 50% by mass, more preferably 1 to 45% by mass and still more preferably 2 to 40% by mass.

The alcohol which can be used may include, for example, ethanol, 1-propanol, 2-propanol, 1-butanol, 2-butanol, 2-methyl-1-propanol, 2-methyl-2-propanol, 1-pentanol and 3-methyl-3-methoxybutanol.

The amount of the solvent in the slurry can be selected according to the uniformity of the permeation layer formed, the thickness of the layer and the economical point of view and is preferably 10 to 5,000 parts by mass, more preferably 50 to 1,000 parts by mass and still more preferably 100 to 300 parts by mass relative to 100 parts by mass of the porous material.

It is preferable that the slurry further contains a binder in view of improving the strength of the formed permeation layer. The binder may be a component which can provide a binding property so as to form the layer of the porous material on the separating medium layer. The binder may include inorganic binders such as gypsum and colloidal silica; organic binders such as organic fibres, e.g. microfibrillated cellulose; thickeners, e.g. alkaline hydrosoluble copolymers, hydroxyethyl cellulose and carboxymethyl cellulose; polyvinyl alcohols and acrylic acids. One or more binders may be used.

The amount of the binder in the slurry can be appropriately selected according to the type of the binder in view of the strength of the formed permeation layer and an appropriate ascending speed of the mobile phase in the permeation layer from the separating medium layer. For example, when gypsum is used, the amount of the binder is preferably 0.1 to 50 parts by mass, more preferably 0.5 to 30 parts by mass and still more preferably 1 to 20 parts by mass relative to 100 parts by mass of the porous material. When an organic binder is used such as carboxymethyl cellulose, the amount of the binder is preferably 0.1 to 50 parts by mass, more preferably 0.5 to 10 parts by mass and still more preferably 1 to 5 parts by mass relative to 100 parts by mass of the porous material.

When the permeation layer contains the porous material as a constituent and spots are detected by means of the optical responsiveness by the irradiation of ultraviolet rays, the optical responsiveness can be conferred to the permeation layer by adding the fluorescent indicator to a slurry containing the porous material. The fluorescent indicator can be well known fluorescent indicators and may include, for example, magnesium tungstate, manganese-containing zinc silicate and the like described above. The amount of the fluorescent indicator can be selected within the range that allows the separation of the target substance and, generally, it is preferably, relative to 100 parts by mass of the porous material, 0.1 to 10 parts by mass and, in order to obtain an optimal contrast between the target substance and the permeation layer, 1 to 8 parts by mass.

When the permeation layer contains the porous material as a constituent and in order to detect spots of the target substance in a sample by colour development reactions, optical responsiveness can be conferred to the permeation layer by adding the chromogenic reagent to a slurry containing the porous material. The chromogenic reagent may include well known phosphomolybdic acid, ninhydrin and the like. The amount of the chromogenic reagent can be selected within the range that allows the separation of the target substance and, generally, it is preferably, relative to 100 parts by mass of the porous material, 0.1 to 10 parts by mass and, in order to obtain an optimal contrast between the target substance and the permeation layer, 1 to 8 parts by mass.

The target substance in a sample can be separated and detected on the TLC plate of the present invention by following the conventional method of use of TLC plates.

The target substance in a sample can be separated and detected by the method comprising the steps of developing the sample along the development direction (which is preferably, when the TLC plate has a rectangular shape for example, a longitudinal direction) of the TLC plate with a mobile phase, drying the mobile phase on the TLC plate, and detecting the migrated spots of the components of the target substance by the irradiation of ultraviolet rays or colour development treatment with the chromogenic reagent.

By developing the sample on the TLC plate of the present invention with a mobile phase, the target substance in the sample is separated and, simultaneously, the target substance permeates into the permeation layer on the separating medium layer.

The target substance as used herein has an optical responsiveness that is different from that of the permeation layer and has the same optical responsiveness as that of the separating medium layer.

The TLC plate of the present invention allows the separation and optical detection of a raffinate component and an extracted component of a target substance in a sample on one TLC plate. Conventional TLC plates having two separating medium layers had an issue such that spots may be broad due to the difference in the migration speed of the respective components in a target substance in a sample in each separating medium layer. However, the present invention does not result in this problem and secures the detection of both spots of a raffinate component and an extracted component. The present invention also secures the detection of the respective separations of multiple samples which are spotted in series on the TLC plate and developed simultaneously. The components in the target substance can also be isolated by collecting the part (including the separating medium layer) containing a particular spot which has permeated into the permeation layer and carrying out extraction procedures.

EXAMPLES

Example 1

First, 4.00 g of a packing material (hereinafter also referred to as "IA packing material") of CHIRALPAK IA® (Daicel Corporation), 0.60 g of gypsum, 4.00 g of a 2% CMC (carboxymethyl cellulose) 1110 (Daicel Corporation) aqueous solution and 0.60 g of a 20% Snowtex C (Nissan Chemical Industries, Ltd.) aqueous solution were added to a mixed solution of 0.40 g of water and 1.60 g of ethanol and thoroughly stirred while applying ultrasound to prepare a first slurry.

Meanwhile, 4.00 g of silica gel (for liquid chromatography from Daiso Co., Ltd., IR-60-5/20-U), 0.20 g of gypsum, 6.00 g of a 2% CMC (carboxymethyl cellulose) 1110 (Daicel Corporation) aqueous solution and 0.08 g of manganese-containing zinc silicate were added to a mixed solution of 2.02 g of water and 2.80 g of ethanol and thoroughly stirred while applying ultrasound to prepare a second slurry.

The first slurry was uniformly applied on a glass plate using a spreader for TLC plate preparation, and the first slurry layer was air-dried and vacuum-dried at 60° C. for 3 hours while vacuuming with a vacuum pump to stack a separating medium layer of the first slurry. On the separating medium layer was uniformly applied the second slurry using a spreader for TLC plate preparation, and the second slurry layer was air-dried and vacuum-dried at 60° C. for 3 hours while vacuuming with a vacuum pump to form a permeation layer which was a layer of the second slurry on the separating medium layer, thereby preparing a TLC plate 1.

The TLC plate 1 had a width of 5 cm and a length of 10 cm. In the TLC plate 1, the separating medium layer had a thickness of 150 μm and the permeation layer had a thickness of 20 μm.

The separating medium layer of the first slurry corresponds to a layer of the IA packing material and the permeation layer of the second slurry corresponds to a layer of the silica gel. The IA packing material has an average particle diameter of 20 μm and the silica gel has an average particle diameter of 14.4 μm.

An ethyl acetate solution (about 1 μL) containing a 1% racemic substance of Troeger's base (TB) and a 1% racemic substance of flavanone (FLV) was spotted on the TLC plate 1 at about 3.0 cm from the bottom along the longitudinal direction. The TLC plate 1 was placed in a developing vessel, which contained a mixed solvent containing n-hexane and ethanol at a volume ratio of 9:1, with the spot of the sample down, so that the optical isomers of Troeger's base and flavanone in the sample were developed along the longitudinal direction of the TLC plate 1.

After the development, the TLC plate 1 was dried with cool air and irradiated with ultraviolet rays, which revealed pale green spots of the raffinate component RTB and the extracted component ETB of Troeger's base and the raffinate component RFLV and the extracted component EFLV of flavanone respectively on the permeation layer (FIG. 1).

The Rf value of the spots were determined from the position where the sample was spotted on the permeation layer, the position where the developing solution reached and the central positions of the spots, revealing that the raffinate component and the extracted component of Troeger's base had Rf values of about 0.63 and 0.46, respectively and the raffinate component and the extracted component of flavanone had Rf values of about 0.41 and 0.33, respectively.

Example 2

The first slurry prepared in Example 1 was uniformly applied on a glass plate using a spreader for TLC plate preparation, and the first slurry layer was air-dried and vacuum-dried at 60° C. for 3 hours while vacuuming with a vacuum pump to stack a separating medium layer of the first slurry.

On the separating medium layer of the TLC plate was then applied the second slurry by silk screen printing. The silk screen plate used had regular circular openings with a pitch of 1.2 mm and a pore diameter of 0.8 mm (see FIG. 5). The second slurry layer was then air-dried and vacuum-dried at 60° C. for 3 hours while vacuuming with a vacuum pump to prepare a TLC plate 2 containing a permeation layer which corresponded to the layer of the second slurry stacked in a dotted manner on the separating medium layer.

The TLC plate 2 had a width of 5 cm and a length of 10 cm. In the TLC plate 2, the separating medium layer had a thickness of 150 μm and the permeation layer had a thickness of 20 μm. The IA packing material and the silica gel have the same average particle diameter as those in Example 1.

By similar procedures as in Example 1, the optical isomers of Troeger's base and flavanone in the sample were developed along the longitudinal direction of the TLC plate 2.

Figure 2:
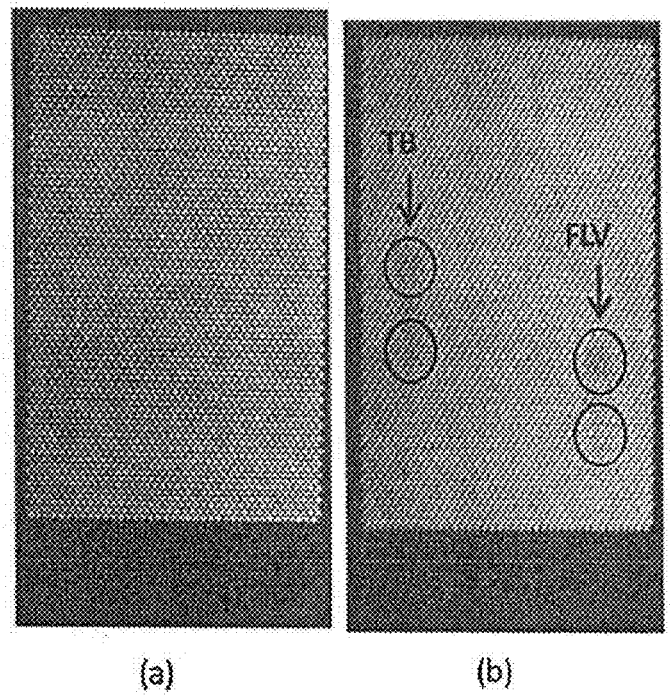
FIG. 2 (*a*) is a view (photographic image) of a TLC plate 2 of the present invention in which a permeation layer is stacked on a separating medium layer in a dotted manner (φ 0.8 mm, Pt 1.2 mm)

After the development, the TLC plate 2 was dried with cool air and irradiated with ultraviolet rays, which revealed pale green spots of the raffinate component RTB and the extracted component ETB of Troeger's base and the raffinate component RFLV and the extracted component EFLV of flavanone on the permeation layer (FIG. 2).

The Rf value of the spots were determined from the position where the sample was spotted on the permeation layer, the position where the developing solution reached and the central positions of the spots, revealing that the raffinate component and the extracted component of Troeger's base had Rf values of about 0.64 and 0.54, respectively and the raffinate component and the extracted component of flavanone had Rf values of about 0.45 and 0.34, respectively.

It was confirmed that when the TLC plate 2 was irradiated with ultraviolet rays, portions where the permeation layer was not stacked, i.e., the separating medium layer appeared to be dark due to the absorption of ultraviolet rays and the TLC plate 2 generally appeared to be darker than the TLC plate 1 upon irradiation of ultraviolet rays (FIG. 2). It was also confirmed that spots of the target substances were more clearly separated in the TLC plate 2 than in the TLC plate 1. Thus, it was confirmed that the TLC plate 2 has a preferable separation property of the target substance.

Example 3

The first slurry prepared in Example 1 was uniformly applied on a glass plate using a spreader for TLC plate preparation, and the first slurry layer was air-dried and vacuum-dried at 60° C. for 3 hours while vacuuming with a vacuum pump to stack a separating medium layer of the first slurry.

The second slurry prepared was the same as the one prepared in Example 1 except that the amount of manganese-containing zinc silicate was 0.16 g.

On the separating medium layer of the TLC plate was then applied the second slurry by silk screen printing. The silk screen plate used had regular circular openings with a pitch of 0.6 mm and a pore diameter of 0.4 mm (see FIG. 5). The second slurry layer was then air-dried and vacuum-dried at 60° C. for 3 hours while vacuuming with a vacuum pump to prepare a TLC plate 3 containing a permeation layer which corresponded to the layer of the second slurry stacked in a dotted manner on the separating medium layer.

The TLC plate 3 had a width of 5 cm and a length of 10 cm. In the TLC plate 3, the separating medium layer had a thickness of 150 μm and the permeation layer had a thickness of 20 μm. The IA packing material and the silica gel have the same average particle diameter as those in Example 1.

By similar procedures as in Example 1, the optical isomers of Troeger's base and flavanone in the sample were developed along the longitudinal direction of the TLC plate 3.

Figure 3:
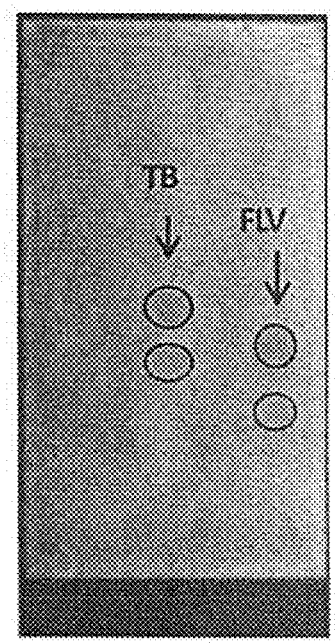
FIG. 3 is a view (photographic image) showing spots of Troeger's base and flavanone developed on the TLC plate 3 of the present invention in which a permeation layer is stacked on a separating medium layer in a dotted manner (φ 0.4 mm, Pt 0.6 mm)
Figure 4:
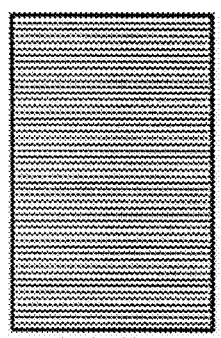
FIGS. 4 ((1) to (4)) is a diagram showing examples of the permeation layers stacked as a series of strips in the TLC plate of the present invention.
Figure 4:
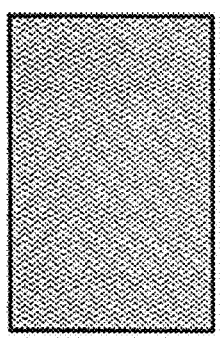
Figure 4:
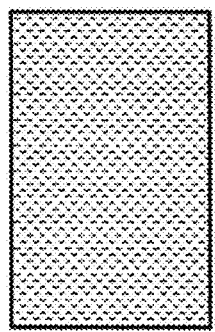
Figure 4:
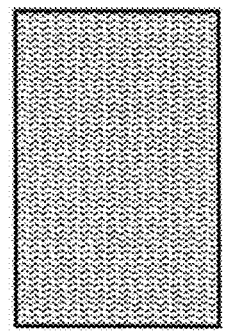

After the development, the TLC plate 3 was dried with cool air and irradiated with ultraviolet rays, which revealed pale green spots of the raffinate component RTB and the extracted component ETB of Troeger's base and the raffinate component RFLV and the extracted component EFLV of flavanone on the permeation layer (FIG. 3).

The Rf values of the spots were determined from the position where the sample was spotted on the permeation layer, the position where the developing solution reached and the central positions of the spots, revealing that the raffinate component and the extracted component of Troeger's base had the Rf values of about 0.56 and 0.45, respectively and the raffinate component and the extracted component of flavanone had the Rf values of about 0.47 and 0.34, respectively.

The TLC plate 3 did not appear to be as dark as TLC plate 2 upon irradiation of ultraviolet rays and thus spots of the target substance were more clearly visualized.

This may be due to the permeation layer being stacked at a decreased pitch.

It was also confirmed that in TLC plate 3 the spots of the target substance appeared to be more circular than those in the TLC plate 1. Thus it was confirmed that the TLC plate had a preferable separation property of the target substance.

TLC has been conventionally used as means for studying separation conditions in column chromatography and also for isolating target substances. The present invention allows more reliable and simple detection, compared to the conventional technique, of the separation of target substances when the separating media are used with compounds for which the detection of the separation by means of optical responses has been difficult. Therefore, it is expected that the present invention contributes to a further expansion of the applications of such separating media and further development in separation and purification techniques using such separating media.

What is claimed is:

1. A TLC plate comprising:
a substrate;
a separating medium layer stacked on the substrate; and
a permeation layer stacked on the separating medium layer and allowing permeation of a target substance separated in the separating medium layer, wherein
the separating medium layer has a separating property for the target substance and optical responsiveness for ultraviolet rays, and
the permeation layer has an optical responsiveness different from that of the separating medium layer and is discontinuously stacked with respect to the separating medium layer along a development direction of the TLC plate.

2. The TLC plate according to claim 1, wherein the permeation layer contains a porous material as a constituent.

3. The TLC plate according to claim 2, wherein the porous material is silica gel.

4. The TLC plate according to claim 1, wherein the separating medium layer contains, as a separating medium, a separating medium for an optical isomer.

5. The TLC plate according to claim 4, wherein the separating medium for an optical isomer is a polysaccharide derivative having hydroxy or amino groups partly or totally replaced by any of an aromatic ester group, an aromatic carbamoyl group, an aromatic ether group and a carbonyl group.

6. The TLC plate according to claim 5, wherein the permeation layer comprises a porous material having a pore volume of from 0.1-0.9 ml/g, a particle diameter of from 0.1-100 μm and is selected from the group consisting of silica gel, zeolite, cellulose, diatomaceous earth, molten silica, clay mineral, alumina, zirconia, sepiolite, attapulgite, palygorskite, talc, kaolinite and montmorillonite.

7. The TLC plate according to claim 1, wherein the permeation layer is stacked on the separating medium layer in a dotted manner such that a pitch between dots is 0.05 to 1.2 mm.

* * * * *